US008806127B2

(12) United States Patent  
Brownell et al.

(10) Patent No.: US 8,806,127 B2  
(45) Date of Patent: Aug. 12, 2014

(54) DATA STORAGE DEVICE WITH INTEGRATED DNA STORAGE MEDIA

(75) Inventors: Richard A. Brownell, Lompoc, CA (US); Mitchell Frey, Santa Barbara, CA (US)

(73) Assignee: Genisyss LLC, Goleta, CA (US)

( * ) Notice: Subject to any disclaimer, the term of this patent is extended or adjusted under 35 U.S.C. 154(b) by 830 days.

(21) Appl. No.: 12/605,618

(22) Filed: Oct. 26, 2009

(65) Prior Publication Data

US 2011/0099322 A1   Apr. 28, 2011

(51) Int. Cl.
| | |
|---|---|
| *G06F 12/00* | (2006.01) |
| *G06F 13/00* | (2006.01) |
| *G06F 13/28* | (2006.01) |
| *C12N 5/00* | (2006.01) |
| *B65D 1/34* | (2006.01) |
| *B65D 6/04* | (2006.01) |

(52) U.S. Cl.
 USPC .......................... 711/115; 435/374; 206/557

(58) Field of Classification Search
None
See application file for complete search history.

(56) References Cited

U.S. PATENT DOCUMENTS

| | | |
|---|---|---|
| 3,970,996 A | 7/1976 | Yasaka et al. |
| 5,496,562 A | 3/1996 | Burgoyne |
| 5,756,126 A | 5/1998 | Burgoyne |
| 5,807,527 A | 9/1998 | Burgoyne |
| 5,972,386 A | 10/1999 | Burgoyne |
| 5,985,327 A | 11/1999 | Burgoyne |
| 6,140,936 A | 10/2000 | Armstrong |
| 6,241,689 B1 | 6/2001 | Chard et al. |
| 6,285,285 B1 | 9/2001 | Mongrenier |
| 6,346,886 B1 | 2/2002 | De La Huerga |
| 6,513,720 B1 | 2/2003 | Armstrong |
| 6,726,820 B1 * | 4/2004 | Frazier .......................... 204/451 |
| 6,840,911 B2 | 1/2005 | Sangha |
| 7,142,987 B2 | 11/2006 | Eggers |
| 7,216,802 B1 | 5/2007 | De La Huerga |
| 7,485,499 B2 | 2/2009 | Brewer et al. |
| 2003/0129755 A1 | 7/2003 | Sadler et al. |
| 2004/0101966 A1 | 5/2004 | Davis et al. |
| 2006/0131431 A1 * | 6/2006 | Finn .............................. 235/492 |
| 2007/0116613 A1 * | 5/2007 | Elsener ........................ 422/102 |
| 2008/0069407 A1 | 3/2008 | Kocher |
| 2008/0176209 A1 * | 7/2008 | Muller et al. ..................... 435/2 |
| 2008/0250193 A1 | 10/2008 | Smith |
| 2008/0291744 A1 * | 11/2008 | Hasvold .................. 365/185.33 |
| 2009/0062677 A1 | 3/2009 | Bolonkin |

* cited by examiner

*Primary Examiner* — April Y Blair  
*Assistant Examiner* — Gary W Cygiel  
(74) *Attorney, Agent, or Firm* — McKee, Voorhees & Sease (57) ABSTRACT

An integral digital memory storage device having a standard form factor to be received by and communicating with a computing device and having memory capability for storage of digital data. An integral multiwell DNA sample tray is carried in a body of the memory storage device for protection and exposed by manipulation of the case for receiving DNA samples.

29 Claims, 7 Drawing Sheets

DATA STORAGE DEVICE WITH INTEGRATED DNA STORAGE MEDIA

BACKGROUND

1. Field

This application relates generally to the field of DNA storage and identification, and more particularly to an integrated device with digital storage memory for data and DNA storage in an exposable tray contained within the case of the device.

2. Related Art

DNA and sampling of DNA have become increasingly important in numerous fields from law enforcement and forensic science to species monitoring. With an estimated 400,000 DNA samples taken daily, with many competing forms of both physical DNA and associated data storage, the issues of use, transportation and storage make establishing standardized packages a difficult problem. Physical DNA samples and associated data files have been maintained physically separated due to the storage environment and physical configurations required. Such separate storage is problematic from the standpoint of potential loss or damage of tracking information and high cost of retrieval. With the volume of DNA information being retained, the sheer size of information files requires enormous temperature and humidity-controlled environments for file storage at significant cost to maintain. Additionally cold DNA storage requires complex facilitization and significant energy consumption.

As exemplary, the Child Identification safety market is burgeoning with products using such elements as hair clippings or buccal swabs for DNA without sufficient long term storage survivability or reliable matching of associated data. In Forensic science, DNA samples are collected and stored separately from photographs, notes and other physical or digital evidence adding to the complexity of the chain of evidence.

It is therefore desirable to provide for integrated storage of DNA samples and associated data in a room temperature storable device. It is further desirable that the integrated storage system be small and compatible with existing computer and data storage systems.

SUMMARY

Exemplary embodiments provide an integral digital memory storage device having a standard form factor to be received by and communicating with a computing device and having memory capability for storage of digital data. An integral multiwell DNA sample tray is carried in a body of the memory storage device for protection and exposed by manipulation of the case for receiving DNA samples.

In one configuration the integrated storage unit is housed in a SD form factor flash card. In an alternative configuration, the integrated storage unit is housed in a USB thumb drive case.

A system for storage of DNA and corresponding digital data incorporates a standard form factor case with memory for storage of digital data. An integral DNA sample tray is carried in a body of the case for protection said tray exposed by manipulation of the case for receiving DNA samples. A computer is employed having an interface to receive the standard form factor case and at least one data entry device connected to the computer. Operating software associated with the computer downloads data from the entry device into the memory. The data entry device in various configurations may be a keyboard, a camera, an image scanner, a fingerprint scanner, a network interface and a computer memory.

The various embodiments may be employed in a method wherein a DNA sample is obtained and transferred to the sample tray. The integrated storage unit is inserted into an interface on the computing device and a unique indicia is identified associated with the integrated storage unit. Data associated with the DNA is then input into the computer and downloaded from the computer into the memory of the integrated storage unit. The integrated storage unit is then removed from the computer.

The features, functions, and advantages that have been discussed can be achieved independently in various embodiments of the present invention or may be combined in yet other embodiments further details of which can be seen with reference to the following description and drawings.

DETAILED DESCRIPTION

Embodiments of the invention incorporate a structure for DNA and data storage which provides physical media for retaining DNA samples integrally stored within the case of a digital memory device capable of storing accompanying data regarding the samples.

Figure 1:
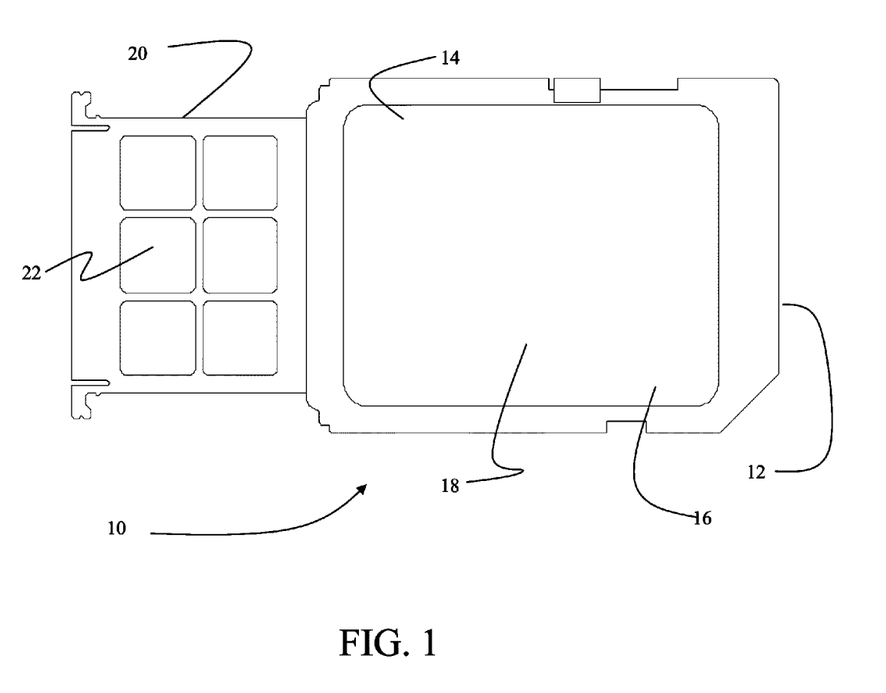
FIG. 1 is a top view of a SD flash form factor implementation of the invention with the multiwell DNA sample drawer in the open position.
Figure 2A:
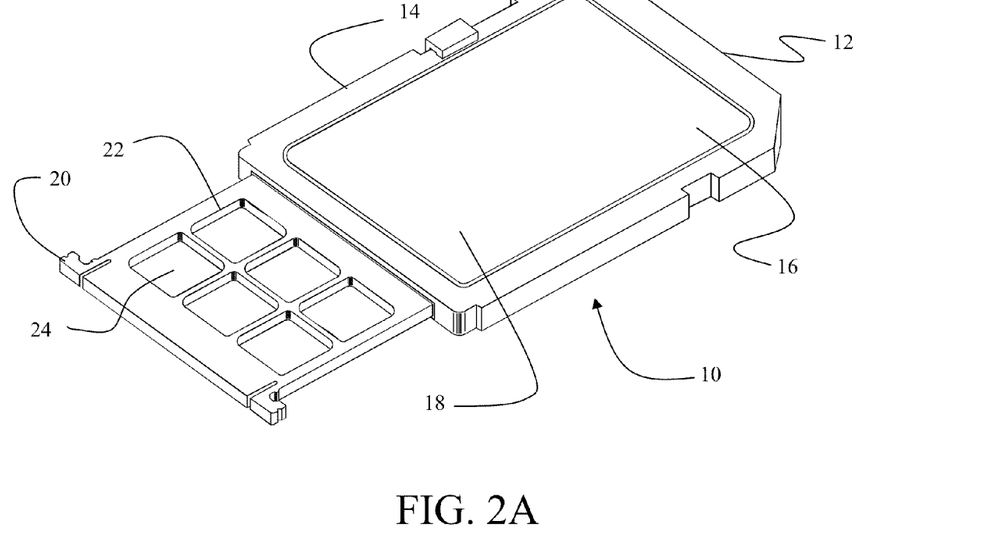
FIG. 2A is an isometric view of the embodiment of FIG. 1 with the sample tray in the open position.
Figure 2B:
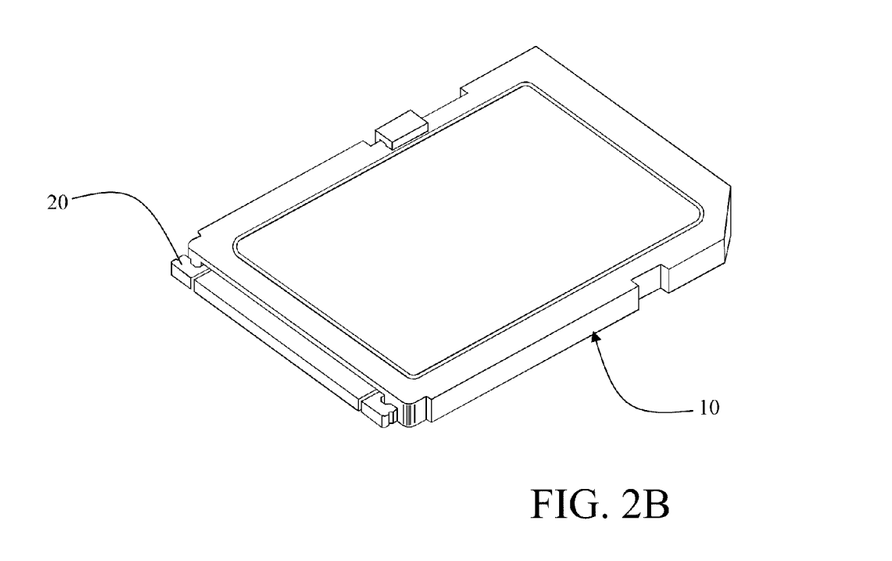
FIG. 2B is an isometric view of the embodiment of FIG. 2 with the sample tray in the closed position.
Figure 3:
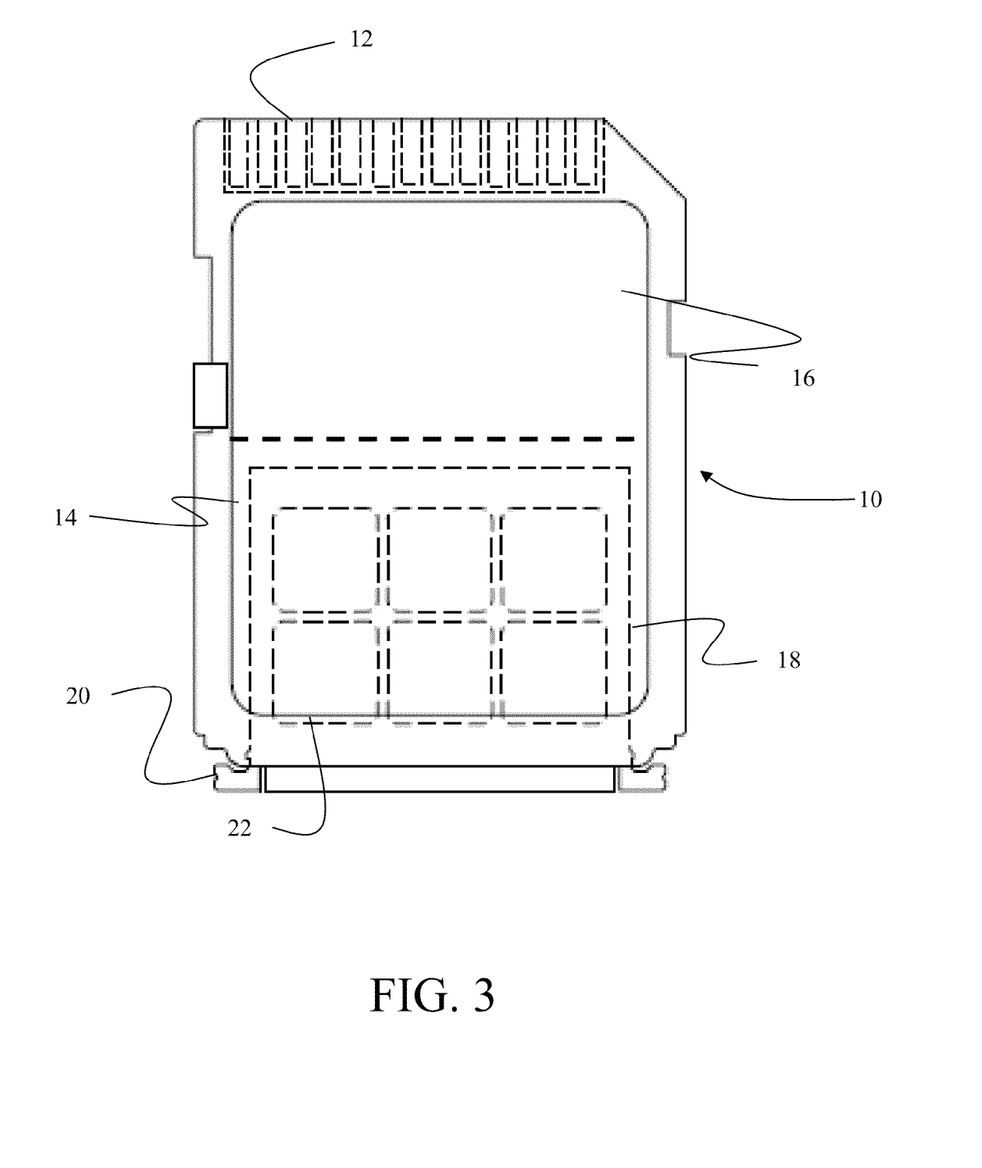
FIG. 3 is a top hidden line view of the embodiment of FIG. 1 with the sample drawer in the closed position and internal details shown.

As shown in FIGS. 1-3, a first embodiment of an integrated digital data and DNA storage unit (the "integrated storage unit") employs a memory device having a form factor to be received in a standard interface for a SD flash card. The flash card 10 has a standard case profile with data transfer pins 12. A body 14 of the card includes portion 16 for the microelectronics for the digital memory and a portion 18 receiving an extendible tray 20. The tray incorporates multiple wells 22 each having a nano-fiber dry storage media (such as FTA® paper available from Whatman Group) 24 for storing of DNA sample which may be applied to the FTA in a conventional manner with the tray in the extended position as shown in FIG. 2A. The tray may then be depressed into the receiving portion of the case to protect the DNA sample media as shown in FIG. 2B. FIG. 3 shows the case in the closed position with the internal details shown in hidden line view. For the embodiment shown, multiple wells are shown for DNA storage in the tray. In alternative embodiments, a single well and/or multiple horizontally or vertically stacked trays with multiple or single wells on one or both sides of the tray may be employed using FTA® paper or other nano-fiber or other room temperature dry storage media for DNA storage.

Figure 4:
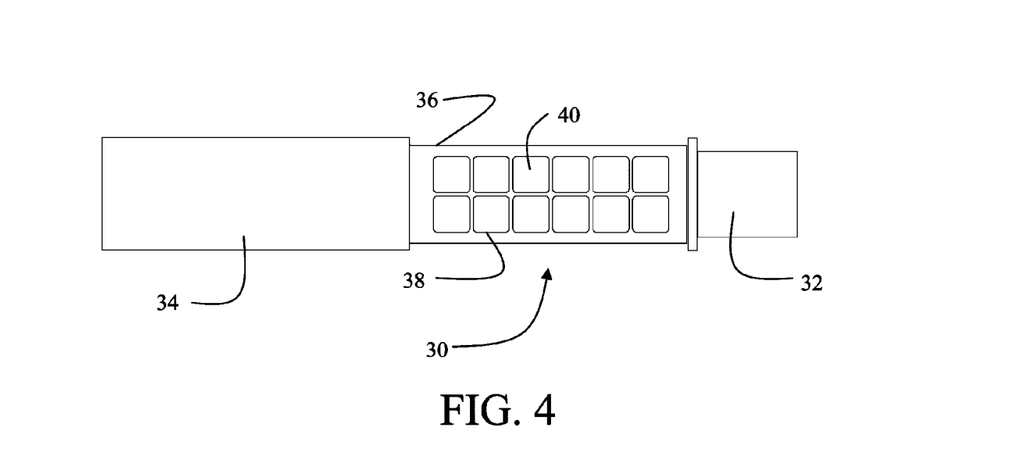
FIG. 4 is a top view of a second embodiment employing a USB thumb drive form factor with the case in the open position.
Figure 5:
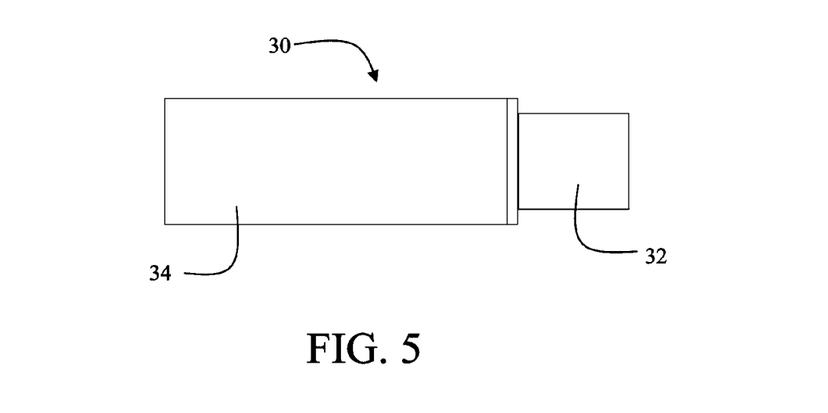
FIG. 5 is a top view of the second embodiment with the case in the closed position.
Figure 6:
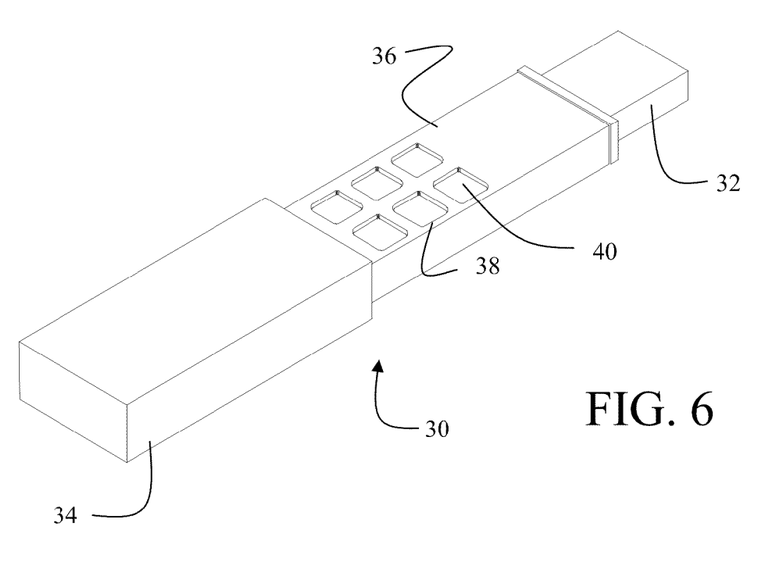
FIG. 6 an isometric view of FIG. 4.
Figure 7:
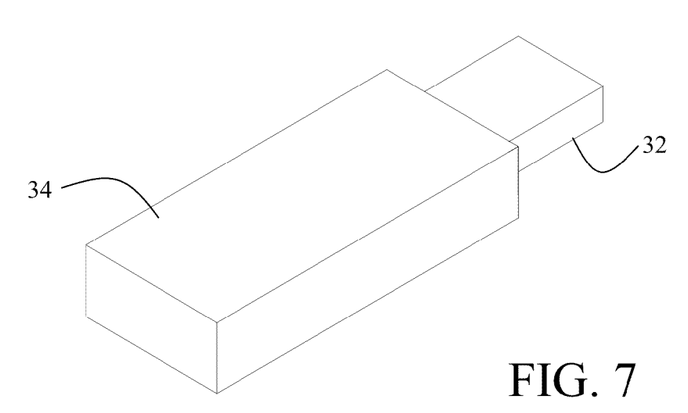
FIG. 7 is an isometric view of FIG. 5.

FIGS. 4-7 show an alternative embodiment wherein the memory device is a standard USB Thumb Drive configuration. The integrated storage unit employs a USB thumb drive 30 which has a standard USB interface 32. As shown in FIGS. 4 and 6, a sliding removable case cover 34 is withdrawn to expose a tray 36 incorporating multiple wells 38 each having a nano-fiber dry storage media (FTA® paper) 40 for storing of DNA sample which may be deposited onto the paper storage media in a conventional manner with the case cover removed. The well cavity is then received into the case cover for complete encapsulation of the paper storage media to protect the samples as shown in FIGS. 5 and 7.

Figure 8:
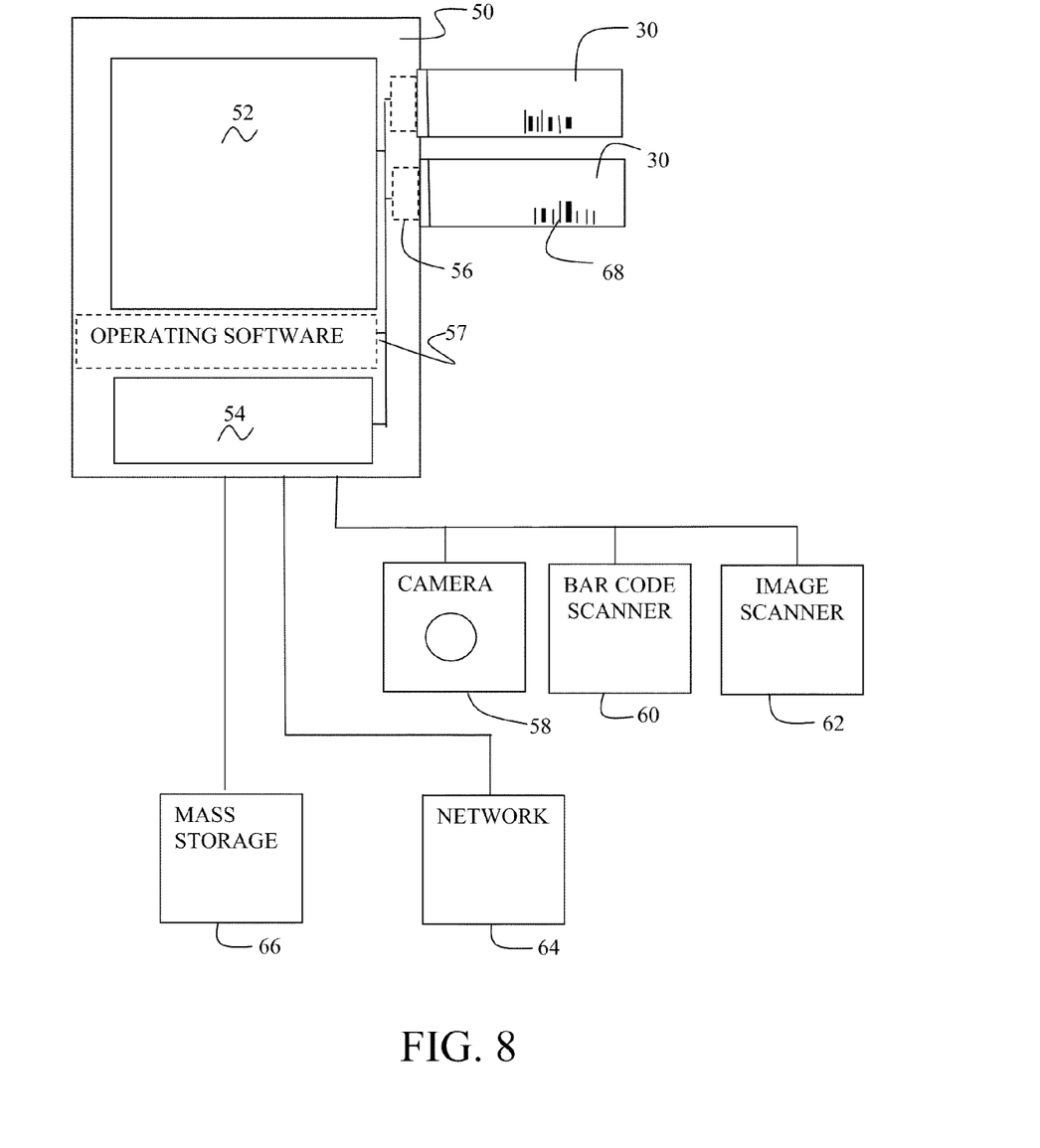
FIG. 8 is a block diagram of a data entry/extraction system employing the integral storage systems as described for the embodiments herein.

FIG. 8 is a block diagram of an operational system for employing the integrated DNA and integrated digital data storage units of the disclosed embodiments. A microprocessor operated device or computer 50 such as a personal digital assistant (PDA), smart phone or laptop having a display 52 and integrated input device 54 such as a keyboard provides operational control of the system. An interface 56 for one or more integrated storage units 30 allows data transfer between the digital data storage unit(s) and the computer using operational software 57 residing on the computer. For the embodiment shown, standard USB interfaces may be employed for the digital data storage units with a configuration as described with respect to FIGS. 4-7 above. Additional peripherals such as a camera 58, bar code scanner 60, image scanner 62 and network interface 64 such as a wireless modem may be provided either as integral elements of the computer 50 or as separate devices interfaced with the computer using standard USB or other interface technology. Mass storage 66 associated with the computer allows integration of control software for specific applications of the digital data storage units as well as temporary or permanent storage of duplicate digital data stored on the integrated storage units. For the embodiment shown, each integrated storage unit 30 employs a bar code 68 for unique identification. The bar code scanner 60 associated with the computer 50 allows easy recognition of the integrated storage unit for data entry or download from/to the computer. In alternative embodiments, integrated digital identification in the digital data storage unit allows identification upon insertion into the interface on the computer or alternative unique readable indicia is provided on the unit.

Exemplary applications the integrated DNA and digital data storage units of the disclosed embodiments with various configurations of the operational system may include child identification kits which could incorporate both a DNA sample bearing master unit, and an identical digital storage device as a traveler, either with additional DNA samples or a non-DNA bearing unit. Hospitals could initiate such child identification by taking samples after birth and entering initial physical descriptive data as well as birth certificate data. Hospitals could insert photographs, finger & feet prints, hospital records and family medical records. Hospitals may keep a duplicate unit on file, providing records for future contact with patient. Similarly, for pets and other veterinary applications DNA sample bearing units may be employed for medical and basic information which contain DNA, medical records, pictures and pedigree information. For breeders of pedigree animals the DNA sample bearing units could be used for demonstrating and storing valuable pedigree history and information. Plant growers may use DNA sample bearing units to allow tracking and storage of hybrid modification information.

Forensic science investigators could employ DNA sample bearing units and operational systems designed for crime scene investigative uses. On-site collection of DNA and related evidence. Data and photographs taken directly from PDA or Laptop computer could be stored on the unit directly with the collected DNA samples. Similarly, in prisons and jail facilities DNA sample units with all related inmate information, records, photographs, etc. could be created upon entry processing and updated with additional data. One unit per individual accommodates following the individual through various facilities.

Individuals and agencies that periodically monitor various species in their natural habitat for endangered species verification and other similar uses could employ DNA sample bearing units with information and photograph storage. The storage units and operational system may be designed to allow for the range of variation in data taken for each species. Similarly, seed and biobanking conducted by universities, organizations, and businesses that are banking genetics for various reasons such as protecting heirloom, and early varieties of plants, seeds, and animals may use DNA sample bearing units designed to store information with each DNA sample.

Figure 9:
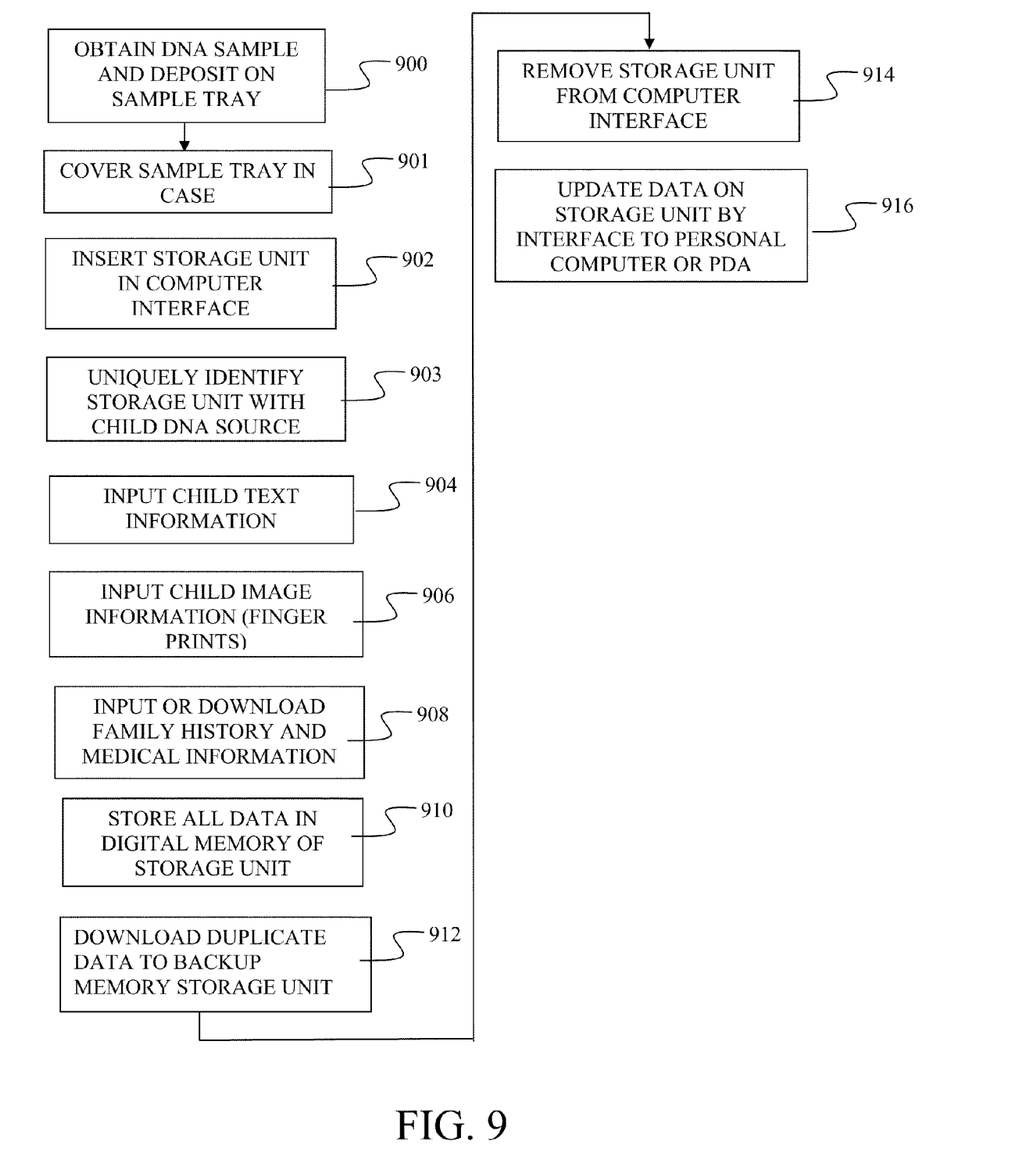
FIG. 9 is a flow chart of an exemplary operational method employed by the system of FIG. 8.

Funeral homes could employ DNA sample bearing units for each decedent, and family history could then be inserted into the data storage. Such integrated storage could provide critical links to prior generations in the event of genetic illnesses or, conversely, if adequately developed, genetic restoration as gene therapy if mutation induced disease was encountered. Similarly, Genealogy societies and members could employ DNA sample bearing units to allow members to archive family DNA & history prior to the death of family members FIG. 9 is a flow chart for an exemplary process to accommodate the first example application of child identification using an operational system as disclosed with respect to FIG. 8. At the hospital at birth or at any other location in a subsequent child identification program DNA is obtained from the child through a blood draw or swab and deposited on the sample tray in an integrated storage unit, step 900. The sample tray is then covered by the case of the integrated storage unit, step 901. The digital data storage unit is inserted into the interface of the computer, step 902 and uniquely identified with the child using a bar code scanner 60 or internal digital identification, step 903. Input of the child's name and other information such as location, date and time of birth, birth weight, length, eye color, birth marks and parent identification are entered on the input device 54 of the computer 50, step 904. Finger, palm and foot prints may be taken in the convention manner and scanned as images into image scanner 60, step 906. In alternative systems, the image scanner may be employed to directly scan the hand and feet for input of identifying prints. Other related data such as family history and medical data may be entered using the input device or downloaded from mass storage 66 or network interface 64 as previously entered data, step 908. All data associated with the child received by the computer 50 is then stored in the digital memory 42 of the integrated storage unit 30, step 910. Duplicate data may then be downloaded into a second integrated storage unit, either with or without DNA storage, as a backup unit or for separate storage, step 912. Additional duplicates may be downloaded when the initial unit is created or subsequently if additional copies of the data are required. The integrated storage unit is then removed from the interface and is available for storage by the parents to maintain personal and identifying information of the child, step 914. Use of standard interfaces allows the integrated storage unit to also be updated with additional data by the parents, doctors, child care or school officials using standard personal computers or other devices equipped with interfacing operating software, step 916. For certain embodiments, any portion of the digital data may be encrypted and/or security protected to avoid overwriting or alteration. For example initial birth data and identifying information could be maintained in a secure portion of the memory with subsequently added data retained in a general purpose or random access portion of the memory.

Having now described various embodiments of the invention in detail as required by the patent statutes, those skilled in the art will recognize modifications and substitutions to the specific embodiments disclosed herein. Such modifications are within the scope and intent of the present invention as defined in the following claims.

What is claimed is:

1. An integral digital memory storage device for storage of DNA samples and digital data associated with the DNA samples, the device comprising:
   a case to be received by and communicating with a computing device;
   memory for storage of the digital data associated with the DNA samples; and
   an integral DNA sample tray, the integral DNA sample tray comprising one or more wells, each of the one or more wells containing a dry storage media to provide dry storage of the DNA samples;
   wherein in a closed position of the integral digital memory storage device the integral DNA sample tray is positioned within a receiving portion of the case thereby encapsulating the integral DNA sample tray and DNA samples stored therein within the case for protection during storage;
   wherein in an open position of the integral digital memory storage device the integral DNA sample tray is exposed to provide access to the dry storage media within the one or more wells to facilitate adding the DNA samples to the one or more wells or removing the DNA samples from the one or more wells;
   wherein manipulation of the case allows for opening or closing the integral digital memory storage device to expose or encapsulate the integral DNA sample tray and DNA samples stored therein.

2. The integral digital memory storage device as defined in claim 1 wherein the dry storage media is a nanofiber dry storage media.

3. The integral digital memory storage device as defined in claim 1 wherein the case is an SD flash card.

4. The integral digital memory storage device as defined in claim 1 wherein the case is a USB thumb drive.

5. The integral digital memory storage device as defined in claim 1 wherein the integral DNA sample tray comprises a drawer retractably received within the case and extendible to receive DNA samples.

6. The integral digital memory storage device as defined in claim 1 wherein the case incorporates a cover removable to expose the integral DNA sample tray.

7. An integral digital memory storage device comprising:
   a SD flash card to be received by and communicating with a computing device and having a case;
   memory in a first portion of the case for storage of digital data;
   an integral multiple well DNA sample tray on a drawer;
   wherein in a closed position the drawer is retractably received within a receiving portion of the case thereby encapsulating the integral multiple well DNA sample tray and DNA samples stored therein within the case for protection during storage;
   wherein in an open position the drawer and the integral multiple well DNA sample tray thereon are extended from the case and exposed to facilitate adding the DNA samples to one or more wells within the integral multiple well DNA sample tray or removing the DNA samples from the one or more wells within the integral multiple well DNA sample tray;
   wherein each well within the integral multiple well DNA sample tray contains a dry storage media to provide for dry storage of the DNA samples.

8. An integral digital memory storage device comprising:
   a USB thumb drive to be received by and communicating with a computing device and having a case with a cover removable to expose a body;
   memory in a first portion of the case for storage of digital data;
   an integral multiple well DNA sample tray on the body to receive DNA samples;
   wherein the integral multiple well DNA sample tray comprises a plurality of wells, each of the wells containing a dry storage media to provide for dry storage of the DNA samples;
   wherein in a closed position of the integral digital memory storage device the integral DNA sample tray on the body is positioned within a receiving portion of the case and the cover is secured in place thereby encapsulating the integral multiple well DNA sample tray and DNA samples stored therein within the case for protection during storage;
   wherein in an open position of the integral digital memory storage device the cover is removed and the integral DNA sample tray on the body is exposed to provide access to the dry storage media within the plurality of wells to facilitate adding the DNA samples to one or more of the plurality of wells or removing the DNA samples from the one or more of the plurality of wells.

9. A system for integrated storage of DNA and corresponding digital data comprising:
   integral digital memory storage device comprising:
      (a) a case with memory for storage of digital data;
      (b) an integral DNA sample tray;
      (c) wherein the integral DNA sample tray comprises one or more wells, each of the one or more wells containing a dry storage media to provide for dry storage of the DNA samples;
      (d) wherein in a closed position of the integral digital memory storage device the integral DNA sample tray is positioned within a receiving portion of the case thereby encapsulating the integral DNA sample tray and DNA samples stored therein within the case for protection during storage;
      (e) wherein in an open position of the integral digital memory storage device the integral DNA sample tray is exposed to provide access to the dry storage media within the one or more wells to facilitate adding the DNA samples to the one or more wells or removing the DNA samples from the one or more wells;
      (f) wherein manipulation of the case allows for opening or closing the integral digital memory storage device to expose or encapsulate the integral DNA sample tray and DNA samples stored therein
   a computer having an interface to receive the integral digital memory storage device;
   at least one data entry device connected to the computer; and,
   operating software associated with the computer for downloading data from the entry device into the memory.

10. The system for integrated storage as defined in claim 9 wherein the at least one data entry device is selected from the set of a keyboard, a camera, an image scanner, a network interface and a computer memory.

11. The integral digital memory storage device as defined in claim 9 wherein the dry storage media is a nanofiber dry storage media.

12. The integral digital memory storage device as defined in claim 9 wherein the case is an SD flash card.

13. The integral digital memory storage device as defined in claim 9 wherein the case is a USB thumb drive.

14. The integral digital memory storage device as defined in claim 9 wherein the sample tray comprises a drawer retractably received within the case and extendible to receive DNA samples.

15. The integral digital memory storage device as defined in claim 9 wherein the case incorporates a cover removable to expose a sample tray.

16. A method for integrated storage of DNA and corresponding digital data comprising:
   providing an integral digital memory storage device for storage of DNA samples and digital data associated with the DNA samples, the device comprising:
   (a) a case to be received by and communicating with a computing device;
   (b) memory for storage of the digital data associated with the DNA samples; and
   (c) an integral DNA sample tray, the integral DNA sample tray comprising one or more wells, each of the one or more wells containing a dry storage media to provide dry storage of the DNA samples;
   (d) wherein in a dosed position of the integral digital memory storage device the integral DNA sample tray is positioned within a receiving portion of the case thereby encapsulating the integral DNA sample tray and DNA samples stored therein within the case for protection during storage;
   (e) wherein in an open position of the integral digital memory storage device the integral DNA sample tray is exposed to provide access to the dry storage media within the one or more wells to facilitate adding the DNA samples to the one or more wells or removing the DNA samples from the one or more wells;
   (f) wherein manipulation of the case allows for opening or closing the integral digital memory storage device to expose or encapsulate the integral DNA sample tray and DNA samples stored therein;
   opening the integral digital memory device by manipulating the integral digital memory storage device to the open position such that the integral DNA sample tray is exposed;
   obtaining a DNA sample and transferring the sample to the dry storage media within the one or more wells of the integral DNA sample tray;
   closing the integral digital memory device by manipulating the integral digital memory storage device to the closed position to thereby encapsulate the integral DNA sample tray and the DNA sample;
   inserting the integrated storage unit into an interface on the computing device;
   identifying a unique indicia associated with the integrated storage unit;
   inputting data associated with the DNA into the computer;
   downloading the data from the computer into the memory of the integrated storage unit; and,
   removing the integrated storage unit from the computer.

17. The method of claim 16 wherein the inputting of data comprises inputting a child's name, location, date and time of birth, birth weight, length, eye color, birth marks and parent identification.

18. The method of claim 17 wherein the step of inputting data further comprises inputting scanned images of finger, palm and foot prints.

19. The method of claim 17 wherein the step of inputting data further comprises inputting family history and medical data.

20. The method of claim 16 wherein the inputting of data comprises downloading data from mass storage.

21. The method of claim 16 wherein the inputting of data comprises downloading data from a network interface.

22. The method of claim 16 further comprising downloading duplicate data into a second integrated storage unit.

23. The method of claim 16 further comprising inserting the integrated storage unit into standard personal computer subsequent to initial inputting of data for updating with additional data.

24. A digital memory storage device for storage of DNA samples and data associated with the DNA samples, the device comprising:
   a case, the case having a body;
   an interface extending from the body for operatively connecting to a computing device;
   a memory for storage of digital data disposed within the body, the memory operatively connected to the interface;
   an integral DNA sample tray carried in the body of the case;
   one or more wells in the integral DNA sample tray; and
   dry storage media disposed within each of the one or more wells of the integral DNA sample tray;
   wherein in a closed position of the digital memory storage device the integral DNA sample tray is positioned within a receiving portion of the case thereby encapsulating the integral DNA sample tray and DNA samples stored therein within the case for protection during storage;
   wherein in an open position of the digital memory storage device the integral DNA sample tray is exposed to provide access to the dry storage media within the one or more wells to facilitate adding the DNA samples to the one or more wells or removing the DNA samples from the one or more wells;
   wherein manipulation of the case allows for opening or closing the digital memory storage device to expose or encapsulate the integral DNA sample tray and DNA samples stored therein;
   wherein the interface is positioned to extend from the body both when the digital memory storage device is in the open position and when the digital memory device is in the closed position of the digital memory storage device.

25. The digital memory storage device of claim 24 wherein the interface is a USB interface.

26. The digital memory storage device of claim 25 wherein the dry storage media is nanofiber dry storage media.

27. A digital memory storage device, the device comprising:
   a case, the case having a body;
   an interface extending from the body for operatively connecting to a computing device;
   a memory disposed within the body, the memory operatively connected to the interface;
   an integral DNA sample tray carried in the body of the case;
   one or more wells in the integral DNA sample tray; and
   dry storage media disposed within each of the one or more wells of the integral DNA sample tray;

the integral DNA sample tray including at least one sample of DNA from an individual;

digital data stored on the memory, the digital data comprising data about the individual;

wherein in a closed position of the digital memory storage device the integral DNA sample tray is positioned within a receiving portion of the case thereby encapsulating the integral DNA sample tray and DNA samples stored therein within the case for protection during storage;

wherein in an open position of the digital memory storage device the integral DNA sample tray is exposed to provide access to the dry storage media within the one or more wells to facilitate adding the DNA samples to the one or more wells or removing the DNA samples from the one or more wells;

wherein manipulation of the case allows for opening or closing the digital memory storage device to expose or encapsulate the integral DNA sample tray and DNA samples stored therein;

wherein the interface is positioned to extend from the body both when the digital memory storage device is in the open position and when the digital memory device is in the closed position of the digital memory storage device.

28. The digital memory storage device of claim 27 wherein the data about the individual includes at least one of name, location of birth, date and time of birth, birth weight, length at birth, eye color, birth marks, and parent identification.

29. The digital memory storage device of claim 28 wherein the data about the individual further includes at least one of a finger print, a palm print, and a foot print.

* * * * *

UNITED STATES PATENT AND TRADEMARK OFFICE
CERTIFICATE OF CORRECTION

PATENT NO.        : 8,806,127 B2                                                          Page 1 of 1
APPLICATION NO.   : 12/605618
DATED             : August 12, 2014
INVENTOR(S)       : Brownell et al.

It is certified that error appears in the above-identified patent and that said Letters Patent is hereby corrected as shown below:

In the Claims:

Col. 7, Claim 16, Line 32:
DELETE after a "dosed"
ADD after a --closed--

Signed and Sealed this
Twenty-first Day of October, 2014

Michelle K. Lee
*Deputy Director of the United States Patent and Trademark Office*